(12) United States Patent
Shepherd et al.

(10) Patent No.: US 10,130,388 B2
(45) Date of Patent: Nov. 20, 2018

(54) POSITION GUIDANCE DEVICE WITH BUBBLE LEVEL

(71) Applicants: New York University, New York, NY (US); The Regents of The University of California, Oakland, CA (US)

(72) Inventors: Timothy M. Shepherd, San Francisco, CA (US); Christopher P. Hess, Mill Valley, CA (US); William P. Dillon, San Francisco, CA (US)

(73) Assignees: NEW YORK UNIVERSITY, New York, NY (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/125,560

(22) PCT Filed: Mar. 13, 2015

(86) PCT No.: PCT/US2015/020426
§ 371 (c)(1),
(2) Date: Sep. 12, 2016

(87) PCT Pub. No.: WO2015/138883
PCT Pub. Date: Sep. 17, 2015

(65) Prior Publication Data
US 2017/0000520 A1 Jan. 5, 2017

Related U.S. Application Data

(60) Provisional application No. 61/952,343, filed on Mar. 13, 2014.

(51) Int. Cl.
*A61B 17/34* (2006.01)
*A61M 25/01* (2006.01)
*A61B 90/00* (2016.01)

(52) U.S. Cl.
CPC ..... *A61B 17/3403* (2013.01); *A61M 25/0105* (2013.01); *A61B 2017/3413* (2013.01); *A61B 2090/068* (2016.02); *A61B 2090/374* (2016.02)

(58) Field of Classification Search
CPC .......... A61B 17/3403; A61B 2090/068; A61B 2090/374; A61B 2017/3413; A61M 25/0105
(Continued)

(56) References Cited

U.S. PATENT DOCUMENTS 5,347,987 A 9/1994 Feldstein et al.
6,097,423 A 8/2000 Mattsson-Boze et al.
(Continued)

OTHER PUBLICATIONS

Search Report and Written Opinion for International Application No. PCT/US2015/020426, dated Jun. 22, 2015, 8 pages.
(Continued)

*Primary Examiner* — Manuel Mendez
(74) *Attorney, Agent, or Firm* — Foley & Lardner LLP

(57) ABSTRACT

A position guidance system for minimally invasive medical procedures includes a medical device having a first end configured for percutaneous insertion and a second end configured to remain exterior to a patient's skin, a hub connection provided at the second end of the medical device, at least one bubble level including a bubble configured to provide a visual indication of a deviation from a target angle for medical device insertion, and a connector configured to reversibly and repeatedly connect the bubble level to the hub connection of the medical device. When the bubble is positioned at a center of the bubble level, an actual insertion angle of the medical device is the same as the target angle. When the bubble is positioned off-center of the bubble level, the actual insertion angle of the medical device deviates from the target angle.

19 Claims, 19 Drawing Sheets

(58) Field of Classification Search
USPC .......................................................... 604/116
See application file for complete search history.

(56) References Cited

U.S. PATENT DOCUMENTS

| | | | |
|---|---|---|---|
| 2004/0087962 A1* | 5/2004 | Gorek | A61B 17/1757 606/96 |
| 2004/0260312 A1 | 12/2004 | Magnusson et al. | |
| 2007/0149878 A1 | 6/2007 | Hankins | |
| 2008/0281156 A1 | 11/2008 | Makower et al. | |
| 2008/0312709 A1 | 12/2008 | Volpe et al. | |
| 2009/0274271 A1 | 11/2009 | Pfister et al. | |
| 2011/0184419 A1 | 7/2011 | Meridew et al. | |
| 2011/0282188 A1 | 11/2011 | Burnside et al. | |
| 2012/0199060 A1* | 8/2012 | Furbush, Jr. | A61B 5/065 116/201 |

OTHER PUBLICATIONS

Howard, M.H., et al., "An Electronic Device for Needle Placement during Sonographically Guided Percutaneous Intervention", Radiology, Mar. 2001, 218(3):905-911.

Idler, C., et al., "Accuracy of percutaneous lumbar pedicle screw placement using the oblique or "owl's-eye" view and novel guidance technology", J Neurosurg Spine, Oct. 2010, 13:509-515.

Jost, G.F., et al., "iPod Touch-Assisted Instrumentation of the Spine: A Technical Report", Neurosurgery, Dec. 2013, 73(2):ons233-ons237.

Kim, E., et al., "CT-Guided Liver Biopsy With Electromagnetic Tracking: Results From a Single-Center Prospective Randomized Controlled Trial", American Journal of Roentgenology, Dec. 2014, 203(6):W715-W723.

Kwan, S.W., et al., "Effect of Advanced Imaging Technology on How Biopsies Are Done and Who Does Them", Radiology, Sep. 2010, 256(3):751-758.

Tiesenhausen, C.V., et al., "A new mobile and light-weight navigation system for interventional radiology", ICE-Elsevier International Congress Series, 2005, 1281:412-417.

International Search Report and Written Opinion in PCT/US2016/057558, dated Dec. 22, 2016, 8 pages.

* cited by examiner

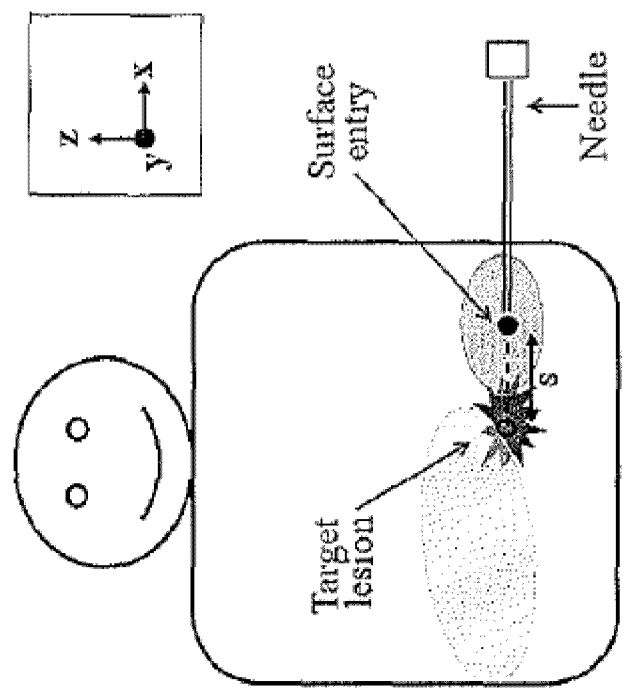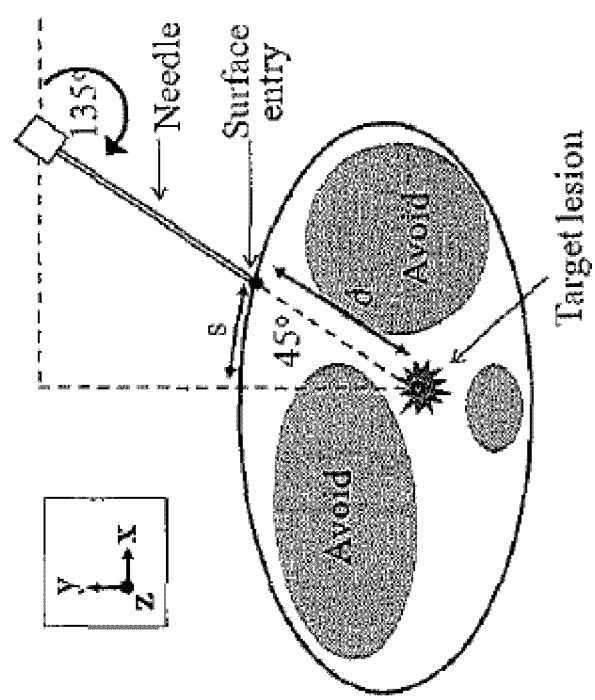
FIG. 3

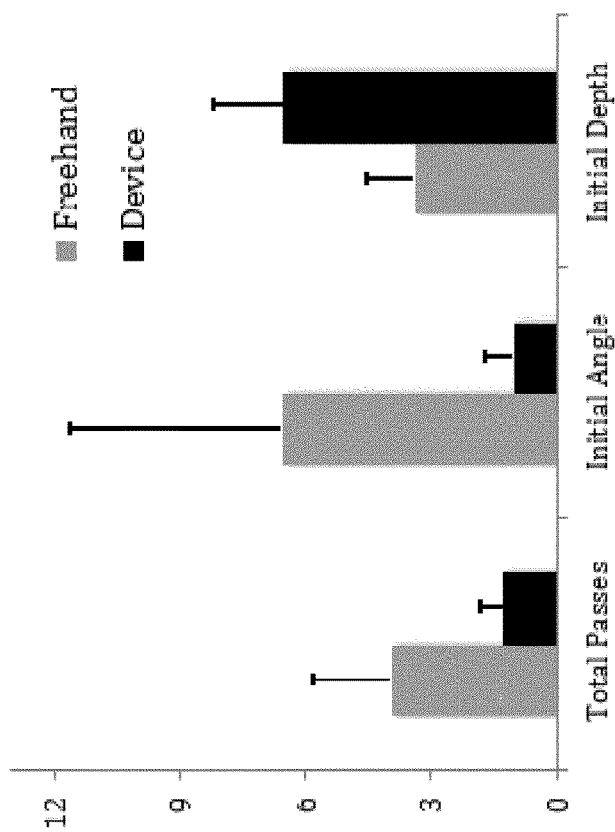

FIG. 13

Improved efficiency using biopsy needle to reach a 5-mm target using 45 angle in tissue phantom [4 subjects, 3 attempts with or without device, mean ± SD]. Note, the y-axis values for initial angle and initial depth are in degrees and cm respectivly. Unpaired t-test indicated statistically significant decreased number of passes to reach the target ($P < 0.0001$), decreased initial angle error ($P < 0.0010$) and increased initial needle placement depth ($P < 0.0001$).

POSITION GUIDANCE DEVICE WITH BUBBLE LEVEL

CROSS REFERENCE TO RELATED APPLICATIONS

The present application is a National Stage of International Application No. PCT/US2015/020426, filed Mar. 13, 2015, which claims the benefit and priority to U.S. Provisional Application No. 61/952,343 filed on Mar. 13, 2014, which is hereby incorporated by reference in their entireties.

FIELD OF THE INVENTION

The present invention relates generally to the field of position guidance devices for minimally invasive medical procedures. More specifically, the present invention relates to a system and method for controlling and using a geometric relationship between a medical device and a bubble level to improve placement.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Minimally invasive medical procedures with image guidance for needle access to anatomic structures are becoming increasingly common and important to the clinical management of patients. As illustrated in FIGS. 1A-1F, image guidance can be used for many different needle-based procedures including CT-guided pulmonary nodule (A), retroperitoneal lymph node (B) or sacral bone biopsies (C). CT-guidance also is demonstrated for a transgluteal abscess drainage (D) and radiofrequency ablation of a right kidney renal cell carcinoma (E). Other image modalities, such as fluoroscopy, also guide needle placement including lumbra puncture (F, AP projection) for cerebrospinal fluid studies, intrathecal chemotherapy or a subsequent CT myelogram. In 2008, the annual rate of image-guided biopsies increased to 1.945 per 100,000 Medicare enrollees (almost 2% per capita). See Kwan et al., "Effect of Advanced Imaging Technology on How Biopsies Are Done and Who Does Them," 256(3) *Radiology* 751 (2010), the entire contents of which are hereby incorporated by reference. For example, the University of California, San Francisco (UCSF) Department of Radiology & Biomedical Imaging currently performs 50-100 image-guided procedures each week. These image-guided procedures generate significant revenue for hospitals and physician practices.

CT image guidance improves visualization of the tissue target during a variety of medical interventions including biopsies, radiofrequency ablations, pain procedures and other interventions. CT-guided procedures are minimally invasive, can reach small deep tissue structures in or surrounded by bone, require minimal patient recovery, decrease healthcare costs and immediately impact clinical management. However, CT-guided procedures still risk inadvertent tissue injury and have longer procedure times than fluoroscopy or ultrasound-guided procedures. Moreover, there may a patient may be concerned regarding the associated radiation use in CT-guided procedures. These potential limitations are mitigated by operator training, skill and experience performing CT-guided procedures. The most common current practice for CT-guided procedures involves iterative readjustment of needle position with focused repeat CT imaging of the patient.

Percutaneous image-guided procedures in which access to inner organs or other tissue is done via needle-puncture of the skin share a common protocol: after initial images are obtained, an operator determines a safe surface entry point, trajectory angle and penetration distance for a manually-directed needle to reach a target organ or tissue. In CT-guided procedures, establishing the best surface entry point for the procedure works well using a standard metallic fiducial and grid (see FIG. 2) and penetration distance is easy to measure with images. For example, FIG. 2 illustrates a typical process for a CT-guided procedure demonstrated for a left L4 transforaminal epidural block for lower back pain. In this procedure, a patient is placed prone, and then CT images are obtained in a region of interest with a radio-opaque grid on a surface of the patient ("$1^{st}$ Scout"). Operators use these images to plan an optimal needle trajectory to reach an anatomic target which includes consideration of needle angle and depth. The surface entry for the needle is verified with a metallic fiducial bead ("$2^{nd}$ Scout"). The operator then places the needle, which is slowly advanced ("Guide") and adjusted as needed using CT guidance until the target is reached and verified with contrast injection ("Contrast"). Although the protocol for establishing a target trajectory angle and penetration distance is common, prescribing and maintaining a correct needle angle is more challenging in daily practice. This is due in part to the fact that image orientations generated by the CT scanner, for example, are relative to the scanner and procedure room floor. Thus, the operator plans the angles with respect to the images, as opposed to planning the angles with respect to the patient who might be positioned in a slight oblique orientation to the scanner or floor to enhance their comfort.

FIG. 3 illustrates an example of an appropriate angle for needle position prior to penetrating the surface of the patient in terms of target angles and horizon angles. In particular, FIG. 3 illustrates a simplified schematic of a typical CT-guided needle biopsy (not drawn to scale). In FIG. 3, the left and right panels demonstrate axial and coronal projections, respectively. In this example, a target must be approached at an angle to avoid other important anatomic structures that are labeled "Avoid"). An angle between the needle trajectory and a vertical line from the target lesion (plumb or perpendicular to the floor) is called the "target angle". In this example, the target angle is 45 degrees. An angle between an opposite needle end (with a hub) and a line parallel to the floor is called the "horizon angle" and should be equal to 180 degrees minus the target angle. In this example, the horizon angle is 135 degrees. In FIG. 3, s is the surface distance from vertical plumb line and d is the depth of penetration to the target.

The current practice is to maintain the target angle in the axial plane while angling in the z-axis is avoided (i.e., the needle remains straight in the coronal projection) as the needle is advanced deeper towards the target. Direct vertical or horizontal orientations for needle placement without oblique angulation are simpler, but have relationships to the floor that the operator also must maintain as the needle is advanced (i.e., horizon angles of 90 and 0 degrees, respectively). Thus, the primary challenge is to prevent or minimize discordance between the planned needle trajectory (see FIG. 3) and an actual needle course throughout the image-guided procedure.

Needle deviations or needle angle errors that occur at or near the skin surface often only become apparent once the needle has traversed deep into the patient. Without any visual reference, the operator may unconsciously alter a correct needle angle or deviate further from the correct needle angle as it is advanced deeply or as the needle encounters tissue interfaces. Correction of a needle angle at depth is only possible for small needle angle errors, as corrections often require withdrawal, adjusted needle angle and reinsertion. This process may require several iterations that further increase tissue injury. Thus, it is critical to get the needle angle correct while the needle is at the surface or only superficially placed within the tissue.

Needle deviations remain common for several reasons. First, the operator must translate angle and depth measurements on the 2-dimensional axial CT images onto an accurate needle target angle on the surface of a patient (with some respiratory motion even when the patient is cooperative). Second, because it is not always possible to view the needle directly orthogonal to the floor or axis of the CT scanner during the procedure, parallax error also can affect true needle position. Third, as the needle is advanced, changes in tissue density (e.g. between fat and muscle) can deflect the needle. The likelihood of encountering error in the actual needle course increases when the target structure is small and/or deeper from the surface, yet these circumstances are often the reason for using image guidance in cases such as a 10-mm retroperitoneal lymph node adjacent to the abdominal aorta 12 cm deep to the surface similar to FIG. 1B.

To minimize error, needle trajectories are planned to be true vertical or horizontal if at all possible. See, e.g., FIG. 1A. When angulated trajectories are necessary to avoid other anatomic structures, the angle is prescribed in only one plane (usually the axial plane as illustrated in FIG. 3) to minimize the potential for compounding error. There are two common ways a needle deviates from the planned trajectory that occur either in isolation or together, hereafter referred to as X-tilt and Z-tilt. As seen in FIG. 4, X-tilt ($1^{st}$ column) occurs when the needle enters the patient too steep (1) or shallow (2) in the axial plane with respect to the planned ideal trajectory (dashed line) to reach the target. Incorrect needle position for X-tilt is recognized in the axial projection, but the other projections usually look normal on images the operator can obtain. For example, subtle needle shortening or lengthening can be difficult to recognize in the coronal projection. Z-tilt ($2^{nd}$ column) occurs when the needle enters the patient with an abnormal angle towards the feet (caudal (3)) or head (cranial (4)) with respect to the planned trajectory. Z-tilt is most evident in the coronal and sagittal projections, but can often be seen in the axial plane when the entire needle is not visualized (e.g. missing superficial needle component in FIG. 1E). These errors are only recognized with imaging in certain planes after they occur.

The magnitude and frequency of needle deviations are subject to an operator's spatial reasoning ability, experience and hand-eye coordination, yet needle position often must be adjusted during the procedure. With the current state of the art, this is an expected component of the procedure at least somewhat mitigated by using image guidance, however the iterative adjustment of needle position and advancement has some disadvantages. Needle placement error can injure anatomic structures leading to undesirable hemorrhage and/or vascular, solid organ or bowel injury. More commonly, needle repositioning increases the volume of tissue traversed by the procedure needle leading to more tissue injury and/or patient pain. Adjustments increase procedure time, which affects patient comfort and the duration of the patient's exposure to conscious sedation, as well as decreased throughput to the detriment of patient wait times and practice revenue. Adjustments also require more imaging, which in the context of x-ray or CT guidance, increases a patient's exposure to ionizing radiation. Finally, the procedure can fail to sample the desired target for treatment or diagnosis.

Many technical solutions have been proposed to improve the safety and efficiency of image guidance during medical procedures over the past 25 years. These include various handheld, stereotactic or robotic devices; augmented visual overlay; and laser, electromagnetic or camera tracking guidance. Although these solutions propose innovative methods for improving the safety and efficacy of image-guided interventions, many of these solutions are expensive or not widely available, and have so far proven difficult to realize widely in clinical practice.

The current state of the art is to direct needle placement using an iterative cycle of needle movement and image guidance, but there is a delay in feedback to the operator from imaging after the needle is manipulated. In typical guidance devices, the device holds the needle and prescribes the angle in that the operator inserts the needle through the device, instead of relying on the operator to keep the angle steady by hand.

Robotic systems have been proposed to be placed next to the patient in the imaging suite, but these are designed more to replace or supplement for an experienced operator rather than enhance their abilities. A separate robotic system may prove cumbersome, complicated, expensive and unable to adjust for patient movement during the procedure without repeat setup imaging. Similarly, "brain lab" navigation systems are in common use, for example, at UCSF for neurosurgery. However these brain lab navigation systems require extensive preoperative imaging, significant computation and modeling prior to procedures with stereotactic equipment. This is inconsistent with the typical patient presentation and workflow for procedures outside brain tumor resection. These systems are expensive to implement and require additional imaging on a separate occasion. Further, unlike the brain, other regions of the body have more periodic movement over the time that would degrade preparative imaging for these systems. Many image-guided procedures also are done on patients who may not be amenable to the highly controlled settings required for the pre-procedure imaging.

Laser fiducials on the needle have been proposed, but these may require a target for the laser projection that may need to be away from the patient or become cumbersome overlying the site of the procedure.

Real-time ultrasound guidance may work, but only on superficial soft tissue anatomic targets in non-obese subjects. Ultrasound-guidance is extremely limited in regions that contain or adjacent to air or bone.

A need exists for improved technology that is more practical and allows for improvement of the precision and speed of image-guided needle placement to minimize the risks of needle deviations from the planned trajectory.

SUMMARY

One embodiment of the invention relates to a position guidance system for minimally invasive medical procedures includes a medical device having a first end configured for percutaneous insertion and a second end configured to remain exterior to a patient's skin, a hub connection provided at the second end of the medical device, at least one bubble level including a bubble configured to provide a visual indication of a deviation from a target angle for medical device insertion, and a connector configured to reversibly and repeatedly connect the bubble level to the hub connection of the medical device. When the bubble is positioned at a center of the bubble level, an actual insertion angle of the medical device is the same as the target angle. When the bubble is positioned off-center of the bubble level, the actual insertion angle of the medical device deviates from the target angle.

Another embodiment relates to a method for using a position guidance system for minimally invasive medical procedures. The method includes selecting a target angle for medical device insertion based on initial images obtained, attaching a bubble level having a bubble configured to provide a visual indication of a deviation from the target angle to a medical device configured for use in a percutaneous image-guided procedure, and adjusting a position of the medical device such the bubble remains in a center of the bubble level. When the bubble is positioned at a center of the bubble level, an actual insertion angle of the medical device is the same as the target angle. When the bubble is positioned off-center of the bubble level, the actual insertion angle of the medical device deviates from the target angle.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which:

FIG. 3 illustrates a schematic of a typical CT-guided needle biopsy.

FIG. 13 illustrates the improved efficiency achieved with use of the position guidance device to reach a 5-mm target using 45 angle in tissue phantom

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 5:
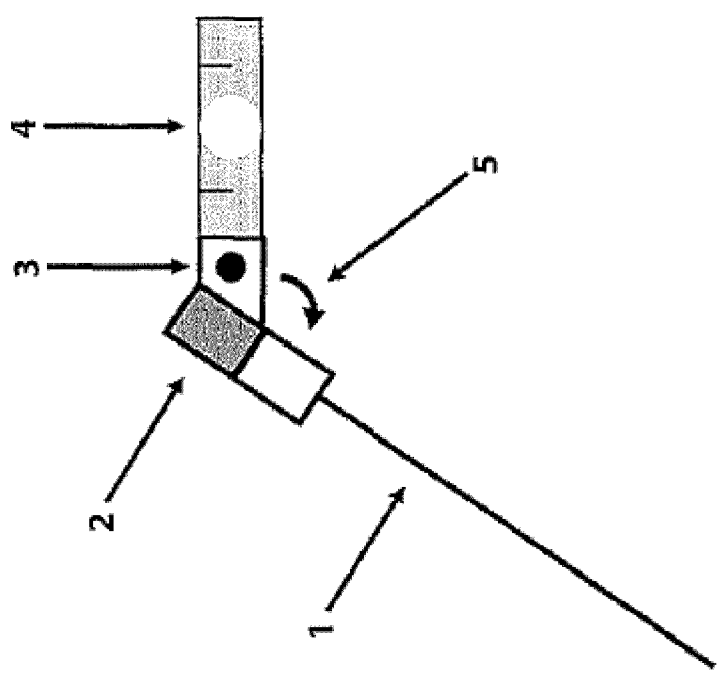
FIG. 5 illustrates an embodiment of a bubble level coupled to a needle.
Figure 15A:
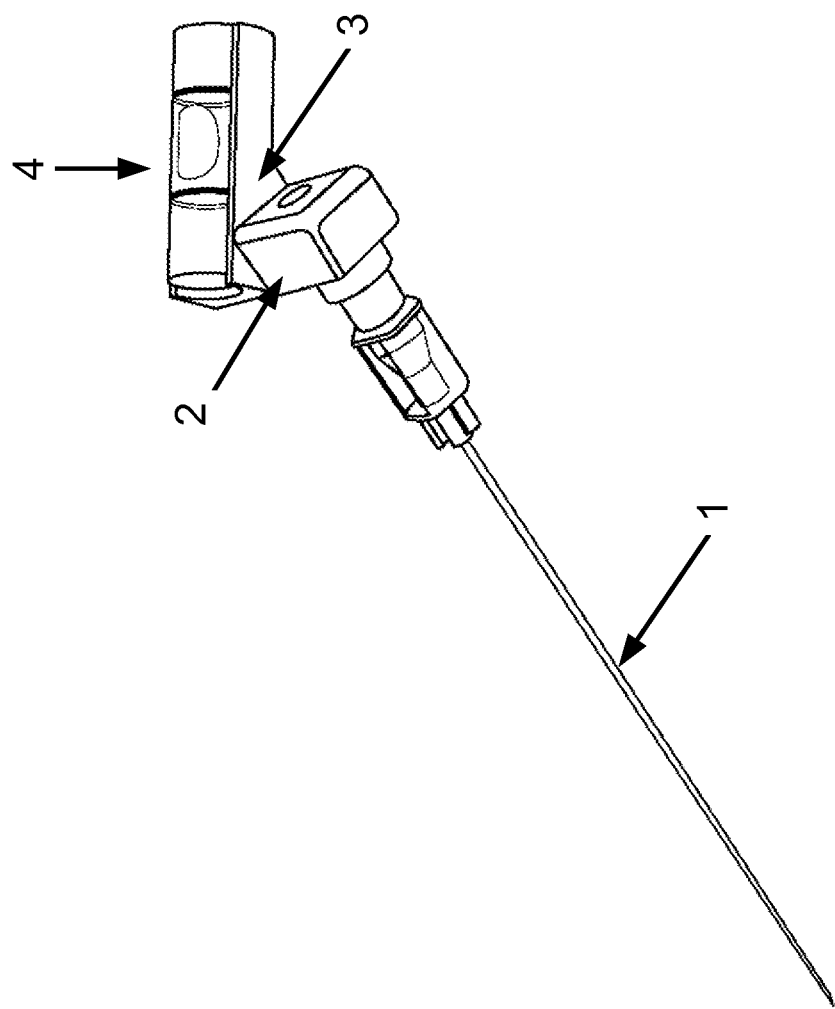
FIGS. 15A and 15B illustrate the bubble level coupled to the needle in the embodiment of FIG. 5 from different perspectives.
Figure 15B:
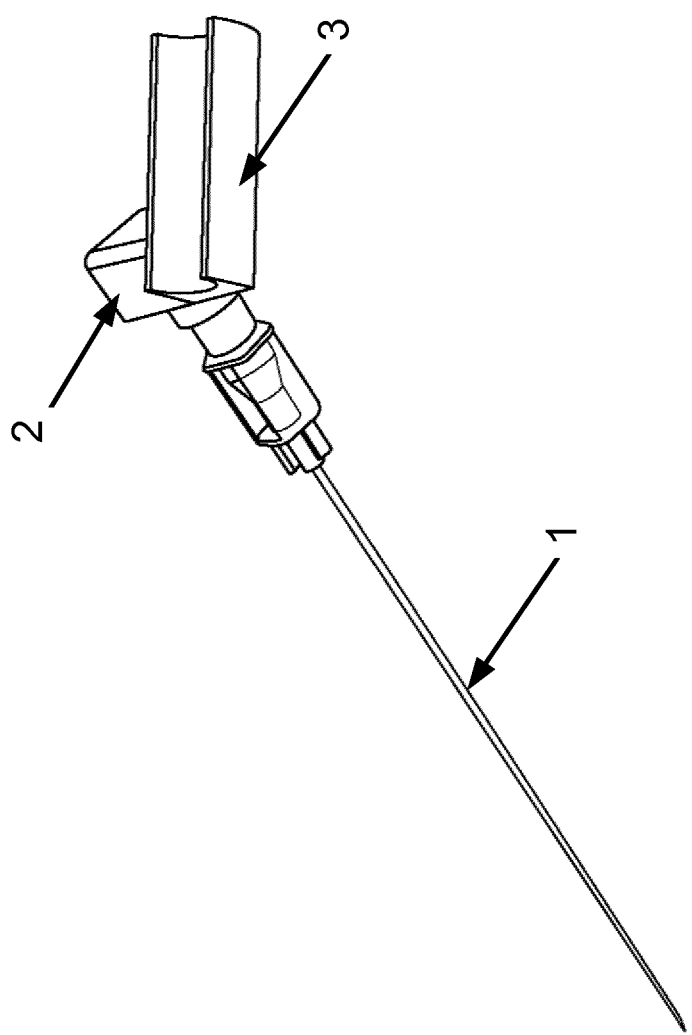

Referring to FIGS. 5, 15A and 15B, a position guidance device 100 includes a bubble level 4 coupled to a medical device 1 via a hub connection 2. A connection 3 between the hub connection 2 and the bubble level 4 can be specified for a particular horizon angle 5 and corresponding target angle. The bubble in the bubble level 4 may be comprised of any fluid. For example, the bubble in the bubble level 4 may be an air bubble. In the embodiments illustrated in the figures, the medical device 1 is a procedure-needle 1. However, one of ordinary skill in the art will appreciate that other medical devices, including, but not limited to probe, biopsy devices or devices for placing surgical and orthopedic hardware may be utilized in place of the needle 1, by coupling the medical device to the bubble level 4 via the connection 3 and/or the hub connection 2. For example, the bubble level 4 may be coupled to a medical device such that the position guidance device 100 is used to provide guidance for stereotactic head frames for spinal correction or patient head positioning in the operating room. Similarly, the position guidance device could be used for alignment of orthopedic hardware in internal or external fixation procedures.

With reference to FIG. 3, which illustrates a horizon angle of 135° and a target angle of 45°, the position guidance device 100 of FIG. 5 will similarly takes advantage of the geometry of parallel lines where the needle 1, will ultimately cross two virtual horizontal lines parallel to the floor that extend through the hub connection 2 and the tissue target, respectively. If a user utilizes the bubble level 4 to maintain a 135° angle (i.e., the horizon angle 5) to the horizontal line outside of the patient, the rule of alternate interior angles results in an angle of the needle 1 relative to the vertical plumb line of 45° (i.e., the "target angle"). By altering or pivoting the angle of the hub connection 2 relative to the attached bubble level 4, multiple target angles can be created. These angles can then be selected by the user for specific, safe skin entry points and courses through the body to the target.

In the embodiments including a needle 1, the needle 1 may be any commercially available needle sterilized for use in a medical procedure and of suitable length to achieve the prescribed penetration depth.

The bubble level 4 may be reversibly and repeatedly coupled to the procedure-specific needle 1 using the hub connection 2. The hub connection 2 may be a Luer-Lock or tuberculin fitting. In other embodiments, the bubble level 4 may be reversibly and repeatedly coupled to the procedure-specific needle 1 via adhesive, hook and loop fastening, threading or a snap system. In most instances, it will be desirable for the bubble level 4 to refrain from blocking the back of the hub connection 2. If the needle 1 is being used for wire access or injections, the extra length obtained via the hub connection 2 would not matter. For coaxial biopsy or therapy systems (e.g. radiofrequency ablation probe insertions), however, the added connector 3 would require a longer inner style device be provided unless the bubble level 4 is removed carefully once the needle 1 reaches the target structure. In some embodiments, the bubble level 4 may be incorporated into the position guidance device 100 by a manufacturer such that the needle 1 and the bubble level 4 are an integral device. In other embodiments, the needle 1 and hub connection 2 may be provided separately from the connector 3 and bubble level 4 such that the operator must assemble the position guidance device 100 prior to use. In other words, the bubble level 4 and the connector 3 may be provided as a separate attachment the directly couples to the hub connection 2 of the needle 1 to indicate the angular relationship between the needle 1 and the horizontal axis or plane respectively.

There are a variety of ways that the specific geometric relationship between the bubble level 4 and the medical device (for example, the needle 1) can be linked. In one embodiment, the bubble level 4 could be a separate piece that is attached via a tubing or hub connection 2 or otherwise adhered to the medical device in a removable and reversible manner. In another embodiment, the bubble level 4 could be incorporated into the medical device (i.e., permanently attached to the medical device).

Figure 9:
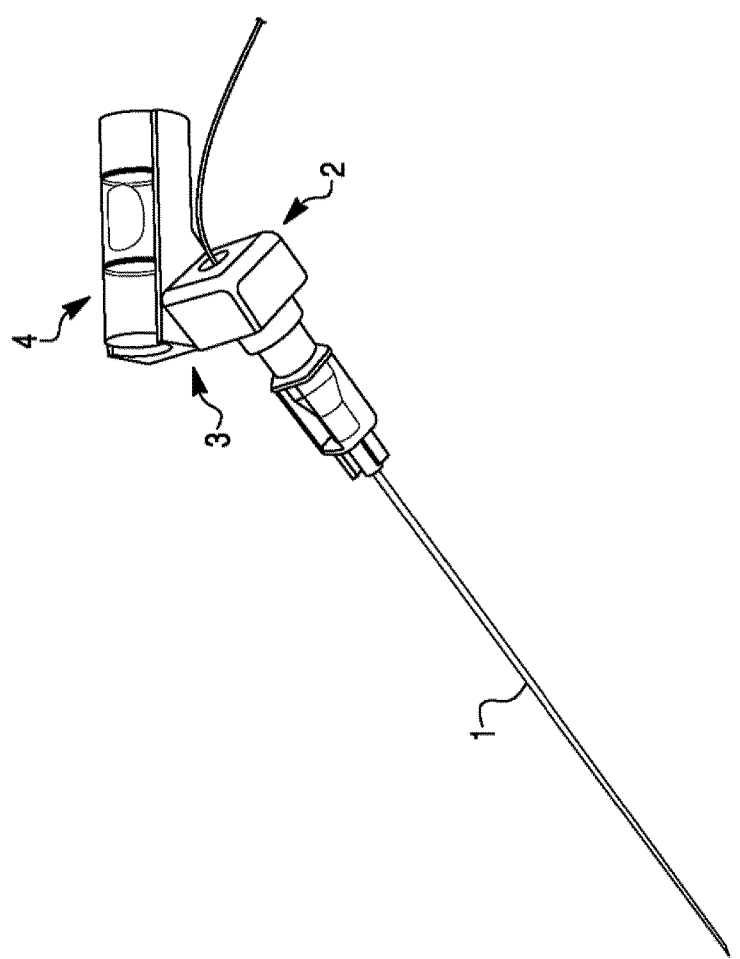
FIG. 9 illustrates an embodiment including a hollow hub connection configured for co-axial passage of wires, inner needles/stylets, other devices or fluids.

The hub connection 2 may be solid or hollow. As seen in FIG. 9, when a hollow hub connection 2 is provided, the hub connection 2 allows for co-axial passage of wires, inner needles/stylets or other devices. Furthermore, this configuration permits injection of fluids or withdrawal of body fluids.

By using the bubble level 4, an operator can correctly identify a true horizontal orientation. In addition, the horizon angle 5 (i.e., a coupling angle between the needle 1 and the bubble level 4) can be varied such that the position guidance device 100 can achieve various target angles. Thus, during needle placement and throughout needle advancement to the target, the operator can focus on visually maintaining a bubble in the bubble level 4 at an appropriate position to correct needle angle until the prescribed penetration depth is reached. For example, the operator can use a centered bubble as a surrogate for correct angle as the needle is advances towards an anatomic target.

The bubble level 4 (also known as a spirit level) is similar to bubble levels typically found in a hardware store in that it includes a vial that is incompletely filled with a liquid such as alcohol such that as the bubble level is rotated, there will always be a bubble of air inside of the vial. When the bubble level 4 is completely horizontal (i.e., level) or vertical (i.e., plumb), the air bubble will be located in the center of the vial. The bubble level 4 is preferably manufactured of a lightweight, sterile plastic with nontoxic chemicals. In addition, the bubble level 4 is preferably MRI-compatible. The sensitivity and range of the bubble level 4 may be varied depending on the identity of the liquid in the vial. For example, the sensitivity and range of the bubble level 4 may be varied depending on the viscosity and surface tension of the liquid in the vial, the volume of the vial, the diameter of the vial, the type of gas comprising the bubble (for example, air or any other suitable gas). In addition, a colorant such as fluorescein, typically yellow or green, may be added to increase the visibility of the air bubble.

Figure 6:
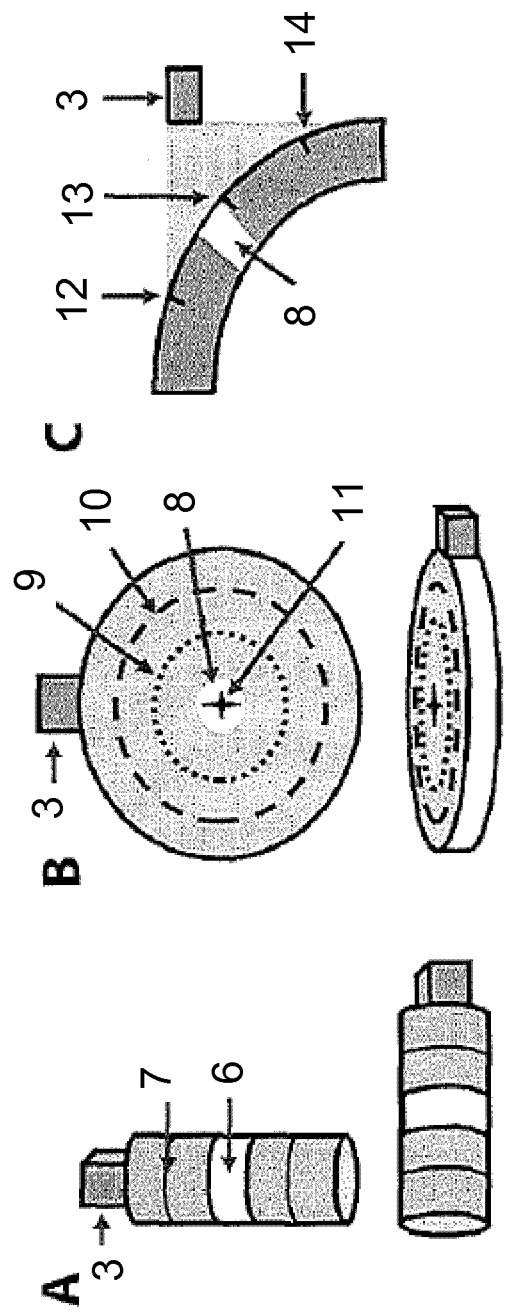
FIGS. 6A-6C illustrates various embodiments of bubble levels to be fixed to a needle.

Referring now to FIGS. 6A-6C, the bubble level 4 may be a tubular bubble level (see FIG. 6A), a bull's eye bubble level (see FIG. 6B) or a dynamic bubble level (see FIG. 6C). The tubular bubble level includes a tubular vial (i.e., housing) having a connection 3 disposed at one end of the tubular vial, a center portion 6, at least one off-center hash mark 7 configured to indicate angle error. A liquid and an air bubble 8 are contained within the tubular vial. The tubular bubble level is configured to detect errors in a needle target angle for one plane depending on a predetermined horizon angle, which will be further described below.

The bull's eye bubble level (also known as a circular bubble) is configured to detect errors for the needle angle simultaneously for two planes. The bull's eye bubble level uses a fixed horizon angle for a predetermined target angle, but can have a pivot added at a junction between the bubble level 4 and the needle 1 to toggle between different horizon angles in the same position guidance device 100. The bull's eye bubble level includes a connection 3 disposed at one end of a housing of the bull's eye bubble level, an air bubble 8 and a liquid contained within the housing, an inner mark 9, an outer mark 10, and a center target 11. In one embodiment, the housing of the bull's eye bubble level is circular and flat-bottomed including liquid (for example, alcohol) under a slightly convex glass face with the center target 11 at the center.

The dynamic bubble level is configured to offer a continuous choice of horizon angles for the operator to use during the procedure. The dynamic bubble level includes a connection 3, a liquid and an air bubble 8 (illustrated at approximately 50 degrees in the dynamic bubble level of FIG. 6C) contained within a housing, and hash marks 12, 13 and 14 provided on the housing for target angles of 30, 45 and 60 degrees, respectively. In other embodiments, the hash marks 12, 13 and 14 may represent different target angle values. The dynamic bubble level has a curved design (i.e., an arcuate vial) that allows the operator to choose any target angle between 0 and 90 degrees for the needle trajectory. Unlike the tubular bubble level and the bull's eye bubble level, The dynamic bubble level can only be viewed from a horizontal perspective.

In operation, the horizon angle of attachment between the needle 1 and the bubble level 4 can be fixed for specific target angles, for example, 45 degrees, and then the operator can prescribe a surface entry and needle course prior to the procedure to accommodate this target angle. In general, a center mark on the bubble level 4 is configured to provide a visual indication of "correct" needle angle position, while air bubble deviation from this mark is configured to provide visual indication of error in angle. For example, in the tubular bubble level illustrated in FIG. 6A, the presence of an air bubble at or proximate to the off-center hash mark 7 may indicate that the actual needle course is too steep or shallow with X-tilt. Off-center hash-marks may also be used to quantify the angle error as the needle 1 is manipulated (i.e., in real time), instead of waiting for repeat imaging to gather position feedback. For example, the air bubble's presence at or proximate to an off-center mark may indicate a minus 5 degree error or 40 degree approach on a position guidance device 100 configured for a target angle of 45 degrees, where the off-center marks are provided in 5 degree increments from the center. In some embodiments, there may be multiple off-center marks to indicate varying degrees of angle error. The sensitivity of angle error may be calibrated based on the physical dimensions and solution properties of the specific bubble level 4. The distance from the center to these quantified error off-center hash marks also may depend on the target angle.

Figure 2:
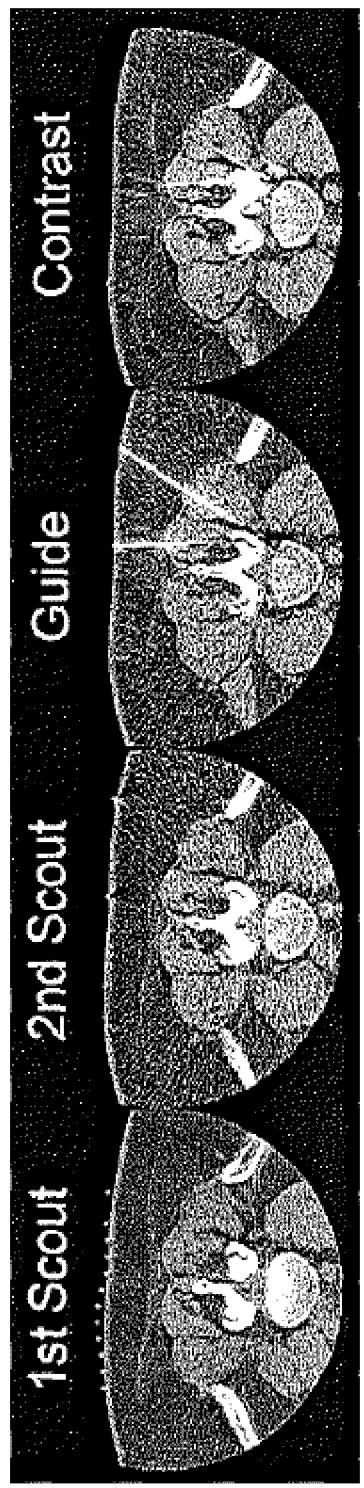
FIG. 2 illustrates a typical process for a CT-guided procedure for a left L4 transforaminal epidural block for lower back pain.
Figure 4:
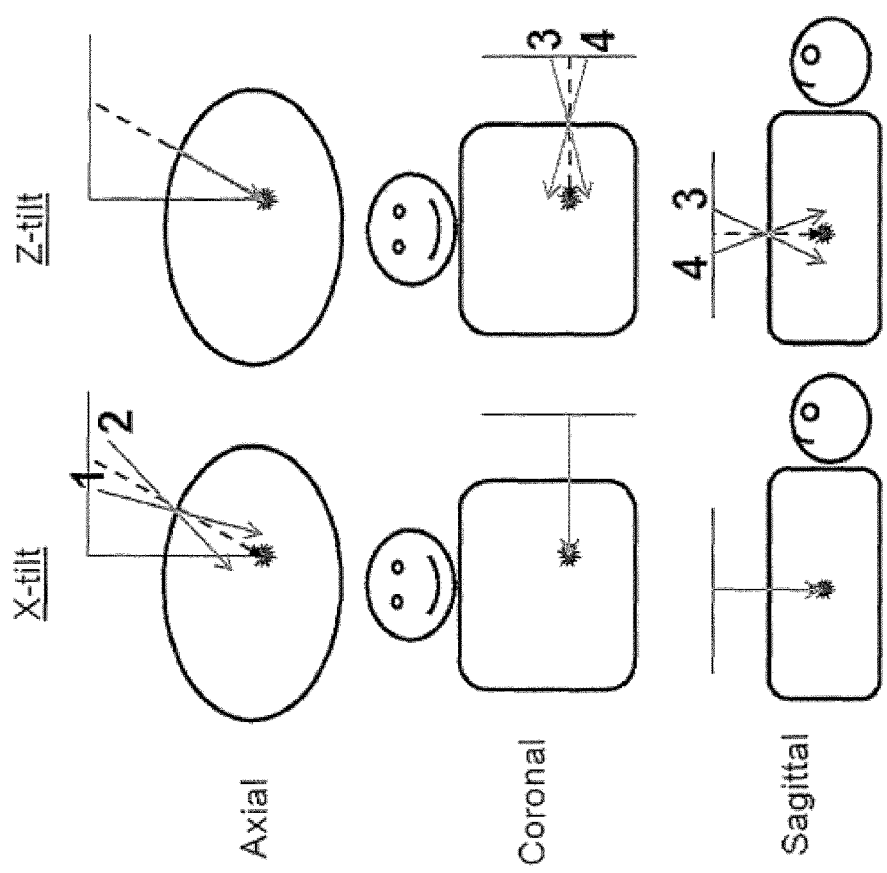
FIG. 4 illustrates X-tilt and Z-tilt errors in needle angle at a surface entry point in an axial, a coronal and a sagittal projection.
Figure 7:
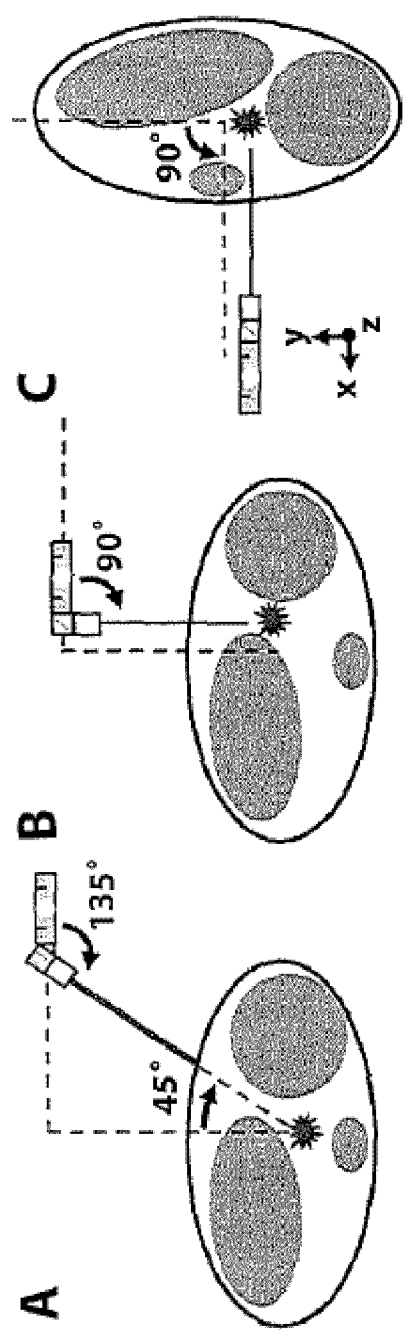
FIGS. 7A-7C illustrate application of a bubble level according to the embodiment of FIG. 5 to angled, vertical and horizontal needle orientations during a CT-guided procedure.

Several commonly used target angles could be manufactured individually for use, for example, 0, 30, 45, 60 & 90 degrees. See for example, FIG. 7. One of ordinary skill in the art will appreciate that certain target angles are used fairly consistently for specific procedures. For example, a target angle of 0 degrees is typically used for a lumbar puncture or facet block. For procedures with less consistent target angles or when individual patient variability may benefit from it, the operator could select a planned needle trajectory that matches one of these target angles based on the initial imaging of the patient and specific anatomic target (i.e. altered surface bead position in the $2^{nd}$ scout image of FIG. 2).

In certain circumstances, individual patient features, such as interposed vital structures, may not be amenable to use of these a priori available manufactured target angles. Under these circumstances, the operator may purposefully use off-center hash-marks to achieve a target angle slightly different than the target angle achieved with the bubble centered. For example, for a 45 degree bubble level, the first hash mark on either side of center may provide target angles deviating from the 45 degree angle by a predetermined number of degrees. For example, if the predetermined number of degrees is 4 degrees, a first off-center hash mark indicates 43 degrees and a second off-center hash mark indicating 47 degrees (i.e., a 4 degree positive or negative angle error). Similar use of the hash marks could be used for the bull's eye device. The dynamic level design achieves this in a different fashion. The off-center hash marks may be used for error feedback or may be intentionally used by the operator to achieve a small range of angles about the set target angle of the position guidance device 100.

In some embodiments, the position guidance device 100 may include a pivot at the connection between the needle 1 and a tubular bubble level 4 such that the position guidance device 100 may toggle between a limited number of specific target angles (such as listed above), or continuously select between 0 and 90 degrees. See FIGS. 7A-7C. In other embodiments, the bubble level 4 may be the dynamic bubble level of FIG. 6C. The dynamic bubble level may be utilized to toggle between a limited number of specific target angles (e.g. 30, 45 and 60 degrees), or continuously select between 0 and 90 degrees. In a case in which the position guidance device 100 includes a pivot or in a case in which the bubble level 4 is a dynamic bubble level, the position guidance device 100 may further include a locking device configured to maintain the desired angle. The desired angle may be prescribed using intrinsic or extrinsic calibration, such as a disposable protractor.

Operation of a position guidance device 100 including a pivot at the connection between the needle 1 and a tubular bubble level 4 is illustrated, for example, in FIGS. 7A-7C. As illustrated in FIGS. 7A-7C, the bubble level 4 may be coupled in an angled, vertical or horizontal orientation to the needle 1 during a CT-guided procedure. The target angles are 45, 0 and 90 degrees in FIGS. 7A, 7B and 7C, respectively. One of ordinary skill in the art will appreciate that FIG. 7A is illustrative for any non-orthogonal target angle between 0 and 90 degrees. As the needle 1 is advanced, the operator may maintain the air bubble in the center portion 6 of the bubble level 4 if the target angle is 45, 0 or 90. Alternatively, the operator may maintain the air bubble at a pre-determined off-center hash mark 7 if the target angle varies from 45, 0 or 90 degrees. As discussed above, off-center bubble positions indicate angle deviation. The tubular bubble level 4 may be viewed form either horizontal or overhead perspectives.

A pivot connection or a dynamic bubble level may be used to vary the target angle throughout the procedure either for error correction based on imaging feedback or to follow a trajectory that circumvents a critical structure. A similar effect may be achieved by switching to another tubular or bull's eye bubble level with a different specific target angle once a particular depth is achieved. For example, the operator may switch from a 45- to a 30-degree target angle bubble level after 5 cm has been traversed. In other words, the bubble level 4 may be uncoupled from the needle 1 by disconnecting the connection 3 of the bubble level 4 from the hub connection 2 of the needle 1.

The off-center error marks of the bubble level 4 may also be used for more exact redirection of the needle 1 once the needle 1 is deep in the tissue. One of ordinary skill in the art will appreciate that the degree and accuracy of needle deflection from the target angle denoted by the off-center error marks will change at certain depths. For example, the off-center error mark may indicate a 10-degree error at the skin surface or within first 5 cm of subcutaneous fat and muscle, but may only indicate a 5-degree angle error once the needle is more than 5 cm deep. These changes may be calculated in phantoms and depth-specific tolerances provided to the operator.

In one embodiment, a single tubular bubble level 4 can be used to detect x-tilt or z-tilt provided that the needle 1 is oriented by the operator perfectly perpendicular to the other axis. See FIGS. 8A and 8B. For the tubular bubble level, in x-tilt, the operator tires to maintain bubble position I throughout needle placement, where bubble positions II and III indicate steep and shallow x-tilt angle errors, respectively. See FIG. 8A. In z-tilt, the operator tries to maintain bubble position IV, where bubble positions V and VI indicate caudal or cranial z-tilt angle errors, respectively. The tubular bubble level can only detect error in one plane unless two bubble levels are combined in orthogonal orientations.

Figure 8:
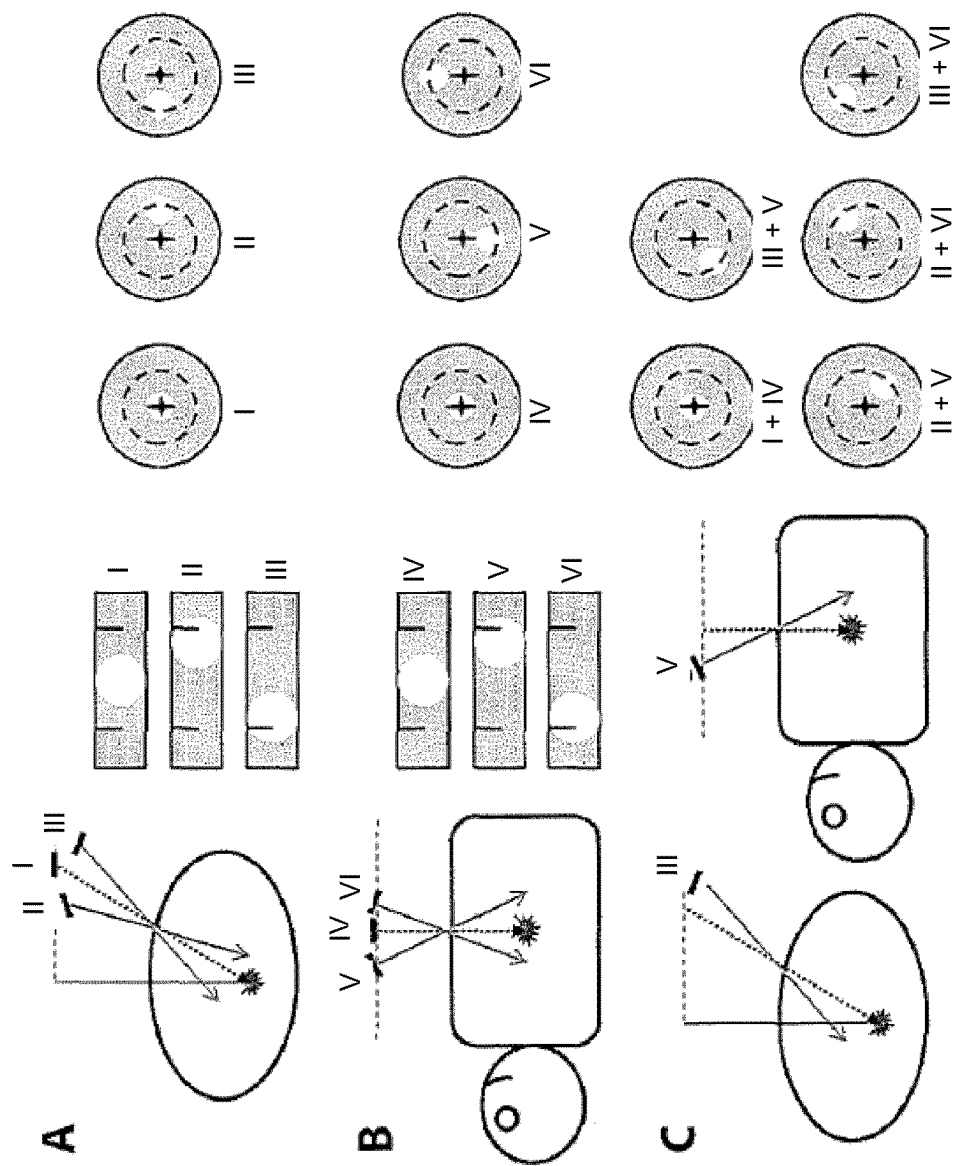
FIGS. 8A-8C illustrate error detection using the bubble levels of FIGS. 6A and 6B for X-tilt error, Z-tilt error or simultaneous X-tilt and Z-tilt error.

In another embodiment, a single bull's eye bubble level may be used to detect x-tilt and/or z-tilt simultaneously from an overhead perspective. An air bubble located at the central target of the bull's eye bubble level is indicative of a correct position or target angle, while an air bubble located at one of the concentric rings is indicative of angle errors of specific degrees (analogous to the hash marks for the tubular bubble level). The orientation of the bull's eye plane relative to the needle orientation would determine the target angle. FIG. 8C illustrates normal bubble position (position I+IV) and feedback from a needle angle that is too shallow (x-tilt) and too caudal (z-tilt), as indicated by position III+V. Examples of other error feed backs are illustrated in the bottom row of FIG. 8C. The bull's eye level is likely to prove highly efficient for pure vertical needle trajectories (target angles of 0 degrees in both the X- and Z-axes) due to the ability to detect x-tilt and/or z-tilt simultaneously form an overhead perspective.

Figure 10A:
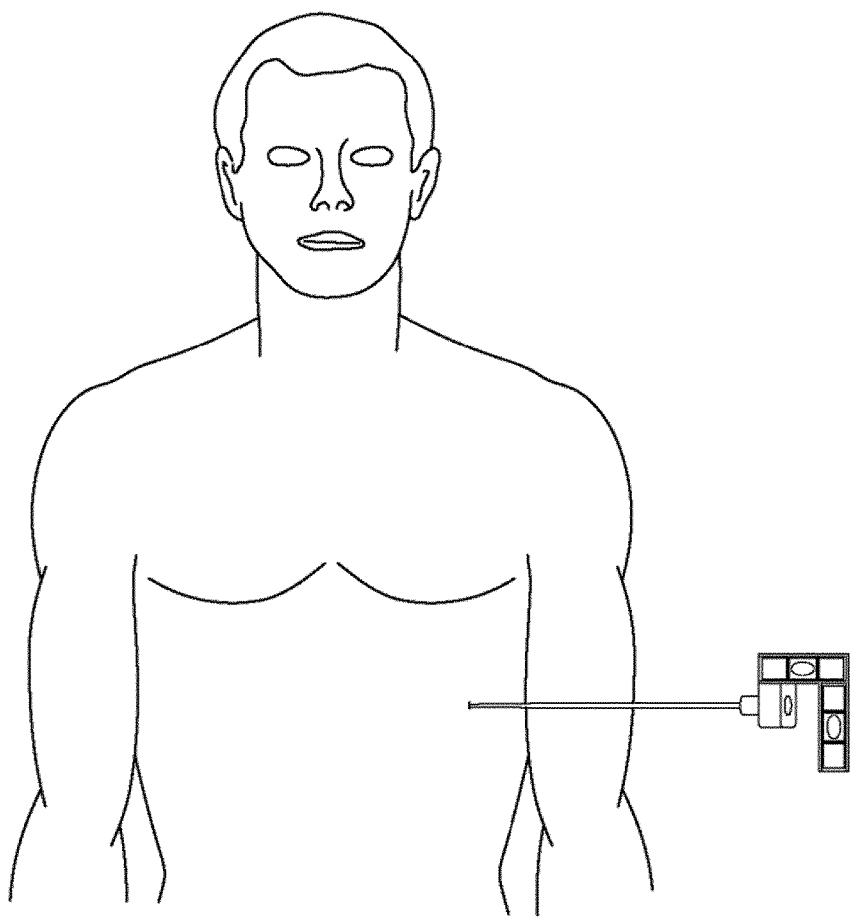
FIG. 10A-10C illustrate an embodiment in which two orthogonally-oriented bubble levels are used to detect both X-tilt and Z-tilt simultaneously from an overhead view from a perspective of an operator performing the procedure (FIG. 10A), a side view of a first bubble level (FIG. 10B), and a 90° side view of a second bubble level (FIG. 10C).
Figure 10B:
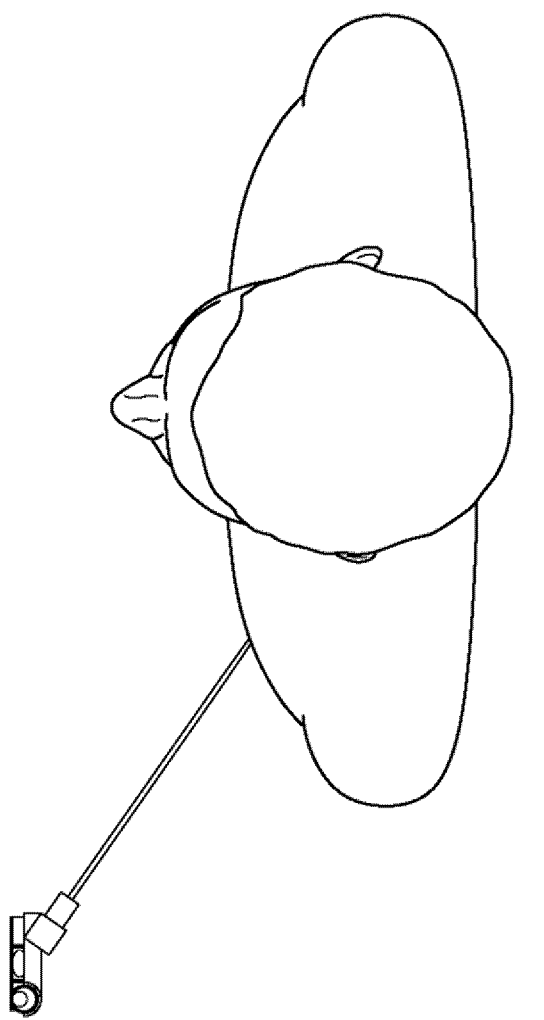
Figure 10C:
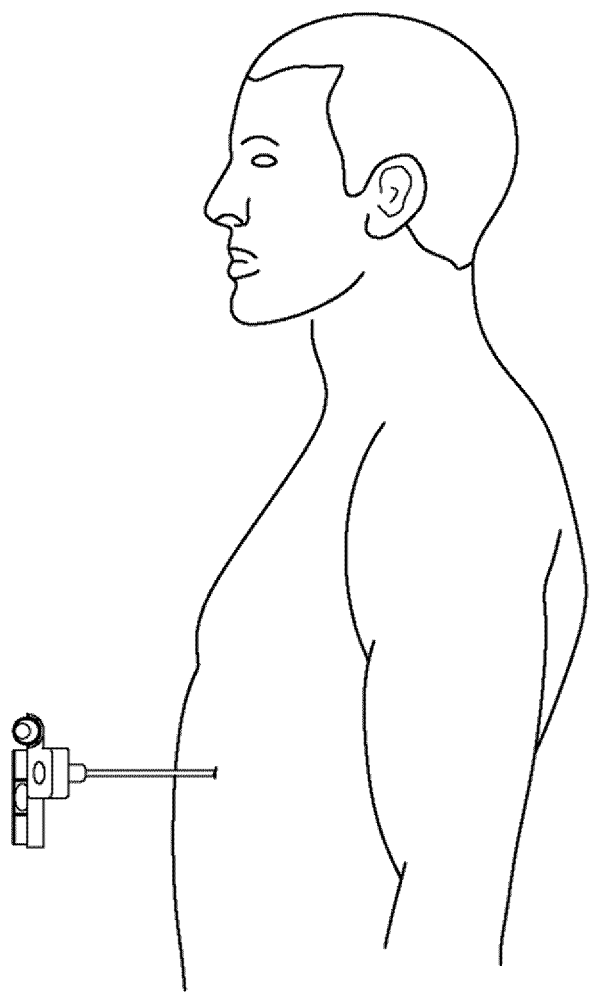

In other embodiments, as illustrated in FIG. 10, two orthogonally-oriented bubble levels 4 can be used to detect both x-tilt and z-tilt simultaneously. FIG. 10A illustrates an overhead view from a perspective of an operator performing the procedure. FIG. 10B illustrates a side view of a first bubble level 4 of the two orthogonally-oriented bubble levels 4. FIG. 10C illustrates a 90° side view of a second bubble level 4 of the two orthogonally-oriented bubble levels 4. This embodiment may utilize two of the same type of bubble level or two different types of bubble levels. For example, in one embodiment, a tubular bubble level may be used to detect z-tilt in combination with a dynamic bubble level used to detect x-tilt. Two orthogonal tubular bubble levels could be viewed from overhead. The target angles for a combination of two bubble level devices could be configured independently of one another. Combinations of bubble levels may be used to detect position and/or position error in two or more planes, simultaneously.

EXPERIMENTAL RESULTS

A prototype of the position guidance system was tested against freehand needle placement by four subjects using a tissue phantom. To construct the prototype, bubble levels (25×7-mm, Level Developments, Ltd., Surrey, UK) were glued to the side of 9-cm 22-gauge spinal needle hubs (below the stylet component) at angles of 150°, 135°, 120°, 90° and 0° to the long axis of the needle measured with a protractor. This produced spinal needles with target angles of 30°, 45°, 60°, 0° (vertical) and 90° (horizontal) relative to the vertical plumb line, respectively. The most ergonomic use of the position guidance device appeared to be for subjects to hold the spinal needle near surface entry with the non-dominant hand and hold the two ends of the level between the thumb and index finger of the dominant hand. The position guidance device was then slowly advanced with real-time adjustment of needle hub position based on the dynamic movement of the bubble within the level. The tissue phantom was constructed from an 10-cm cube of household play-dough (Hasbro, Inc., Pawtucket, R.I.) with a purposefully uneven surface that served as a low-cost model of human tissue properties with similar CT attenuation characteristics. This phantom was placed on a Somatom Definition Edge 64-slice CT scanner bed (Siemens Healthcare, Forchheim, Germany) and then imaged using standard CT parameters (120 kVp, 100 mA, 0.625-mm thick continuous axial slice reconstructions).

Experiment 1

Needle Angle Accuracy

In Experiment 1, four volunteer junior radiology residents (3 females and 1 male with a mean age 28.5±1.3 yrs) with minimal CT-guided needle placement experience were asked to place standard 9-cm 22-g spinal needles into the phantom at different target angles (0, 30, 45, 60 and 90° relative to a vertical plumb line). Three trials were obtained for each of the five angles with and without the bubble level of the position guidance device coupled to the needle hub (30 total passes per subject). The order of target angles freehand or with the position guidance device was random for each subject. For each pass, subjects were asked to place the needle 5 cm deep in one pass at the correct angle. CT images were then obtained to measure needle angles relative to the vertical (0° angle) for each needle placement using a clinical PACS angle tool (iSite, Phillips, Andover, Mass.).

Figure 16:
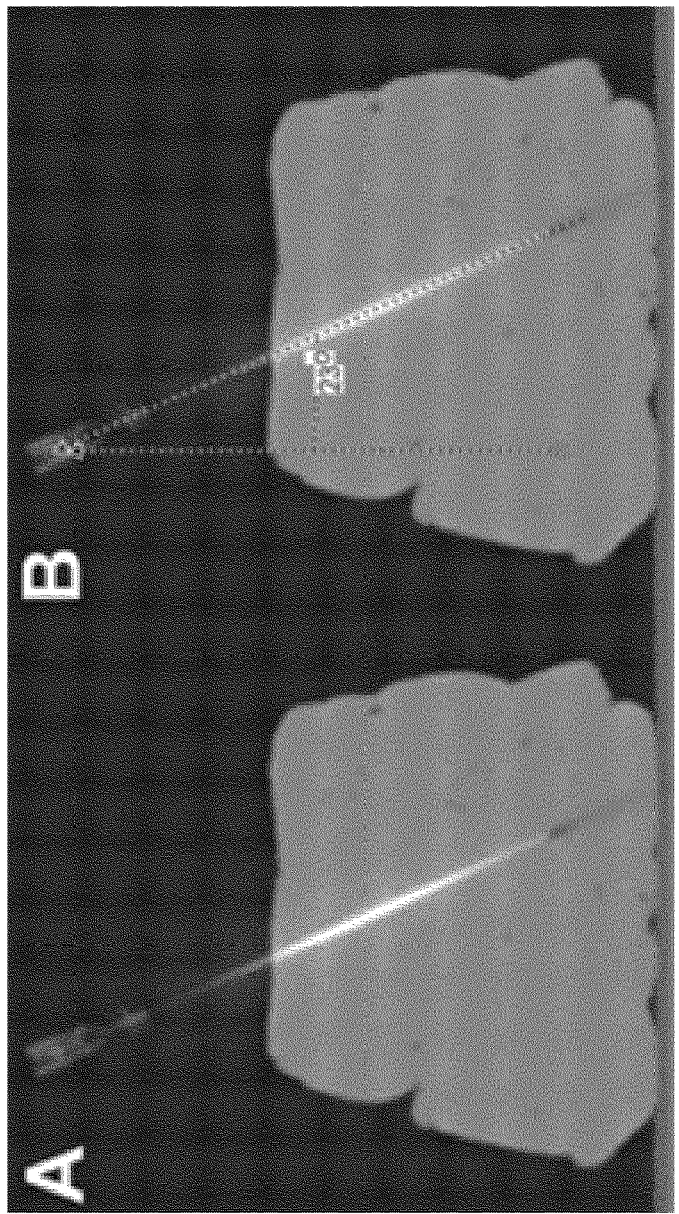
FIG. 16 illustrates an example of a steep needle placement from one of the trials conducted in Experiment 1 with a 30° target angle.

If the difference between the target and achieved angles was a negative value (e.g. 45°−47°=2°, this indicated a shallow needle placement, whereas a positive difference indicated a steep needle placement. For example, in FIG. 16, the subject was asked to insert the needle at a 30° target angle relative to the vertical using a traditional freehand technique. Basic PACS measurement tools demonstrated that on the right cloned image of FIG. 16, the needle was placed 7° too steep. For each subject, the number of perfect placements (0° difference) and the number of negative differences were documented with and without the position guidance device. The absolute value of the difference between target angles and achieved angles with and without the position guidance device was compared using unpaired t-tests. This experiment required approximately 1 hour per subject to complete all 30 passes. There were 120 total passes for the needle angle accuracy experiments: 60 passes without the position guidance device (four users, three trials and five angles) and 60 passes using the position guidance device (four users, three trials and five angles).

Prior to prototype construction, preliminary data for freehand needle placement using the same protocol was obtained from two experienced attending radiologists with 5+ years of experience performing CT-guided procedures. The purpose of this part of the experiment was to understand the degree of angle entry error that highly experienced radiologists might achieve without the position guidance device. This data served as the basis for a post-hoc analysis of how inexperienced residents' use of the position guidance device compared to experienced attendings' use without the position guidance device.

Results of Experiment 1

Experiments using the position guidance device in a tissue phantom demonstrated objective improvements in needle placement accuracy, precision and efficiency. Global comparison between freehand and the use of the position guidance device demonstrated that the position guidance device decreased mean angle error by 68% from 6.6±5.5° to 2.1±2.2° respectively (P<0.0001, unpaired t-test). Global angle error was reduced in all four subjects individually by 50-84%. Note, the standard deviation for angle error also decreased 60% and this is reflected by decreased error bars in all figures for position guidance device-assisted needle placements.

Analysis of individual angles (FIG. 12) demonstrated statistically significant 92%, 86% and 73% reductions in angle error for 30°, 45° and 60° target angles when subjects used the position guidance device instead of attempting a freehand placement. The standard deviation of angle error also decreased 71-74% for these three target angles. There was no statistically significant difference for angle error between freehand and device assisted placement for 0° and 90° target angles.

The position guidance device also increased the number of trials where there was perfect placement, or no difference between the target and achieved angles, from 5% to 30% (18/60 total trials). Mean perfect angle placement incidence increased from 0.8±1.0 to 4.3±2.5 per subject per 15 trials (P=0.0442, unpaired t-test). Further, more than 50% of device trials (31/60 total trials) had 1 degree or less of angle error for the 4 subjects compared to 18% with freehand placement (11/60 total trials).

Secondary analysis examined individual subject tendencies to place the needle too shallow or too steep relative to the target angle. For all four subjects, the number of positive angle errors (i.e. achieved angle less than target angle or the needle was too "steep") decreased from 72% to 45%.

A very limited post-hoc analysis of the attendings' freehand insertion compared to the subjects' (i.e., the junior residents') insertion both with and without the position guidance device demonstrated better free hand needle angle placement accuracy than the junior residents without the position guidance device. When the junior residents used the position guidance device, they were more accurate than the attendings, demonstrating a mean angle error of 0.8 degrees compared to 4.2 degrees, respectively. Angle entry errors from the four subjects (N=4) with or without the position guidance device compared to attendings with 5+ years of experience performing weekly CT guided procedures (N=2) are included in Table 1 below.

TABLE 1

| Angle | Residents freehand | Attendings freehand | Residents with device | P-value+ |
|---|---|---|---|---|
| 0° | 2.3 ± 1.5 | 1.7 ± 0.8 | 3.0 ± 2.8 | 0.435 |
| 30° | 9.8 ± 5.8* | 4.2 ± 3.3 | 0.8 ± 1.6 | <0.001 |
| 45° | 11.1 ± 1.5* | 7.5 ± 4.2 | 1.5 ± 1.2 | <0.001 |
| 90° | 2.2 ± 1.8 | 3.8 ± 2.0 | 3.2 ± 2.8 | 0.340 |

+1-way ANOVA with post-hoc Tuker-Kramer multiple comparisons where the groups that were statistically significant differences to all others denoted with *.

The results show three passes at target angles of 0°, 30°, 45° and 90° for the four residents and the two attendings (mean±SD). The results for the 60° target angle are excluded because the preliminary data for the attendings did not assess the 60° target angle.

Experiment 2

Efficiency of Reaching Target

In a second experiment, the same four subjects were tested individually on the number of passes required to reach a 5 mm gel capsule target approximately 8 cm deep within the tissue phantom with or without the position guidance device. The gel capsule was deliberately placed deep into the tissue phantom so that a 45° angle needle pass could be performed from the contralateral superior surface of the phantom with a penetration depth of 7-8 cm to reach the target. The long axis of the 1.4-cm long capsule was oriented parallel to the long axis of the CT scanner bed ("z-axis"), such that the 5.5-mm diameter cross-section of the capsule presented the effective target in the axial plane. Next a standard grid was place over the superior surface of the tissue phantom and the entry point for a 45° angle approach marked based on preliminary CT images. The subjects were shown the 45° angle on the screen with a line extended from the center of the target beyond the predetermined surface entry point. Then, each of the four subjects was instructed to direct the needle to the target using the minimum number of passes necessary with intermittent CT image guidance. Subjects performed six total trials, alternating between freehand (three trials) or use of the 45° angle position guidance device (three trials). A repeat CT image was obtained after each pass within an individual trial in iterative fashion to demonstrate needle trajectory to the individual performing the needle placement. For each attempt or pass, the subject was shown the needle placement, angle correction if needed and the remaining depth to the target. Once the target was reached, the individual trial was completed. Besides the total number of passes required to reach the target, the entry angle and depth of the first pass were measured with clinical PACS angle and measurement tools. Once the target was reached, the individual trial was completed. This experiment required approximately two hours for all six trials per subject to be completed.

Figure 11:
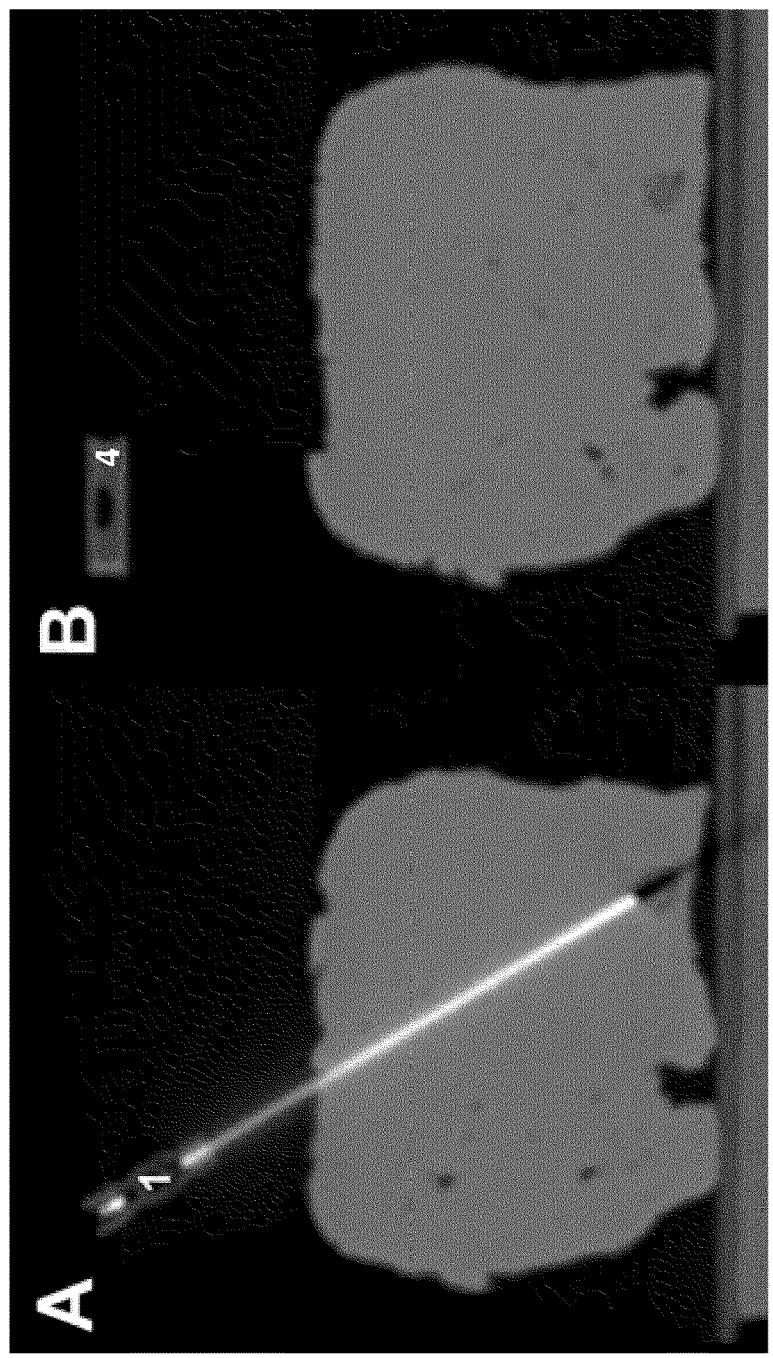
FIG. 11 illustrates results of an experiment using a spinal needle to reach a 5-mm capsule target 8-cm deep within a CT tissue phantom using a bubble level to achieve a 45° angle.

FIG. 11 illustrates an example of the experiment to use a spinal needle to reach a 5-mm capsule target 8-cm deep within a CT tissue phantom using a bubble level attachment to achieve a perfect 45° angle. Panel A demonstrates the needle and panel B the attached bubble level. Because the bubble level is attached to the side, these two components are seen in separate axial CT images. In this second trial with the position guidance device, subject C contacted the center of the target on the first pass by focusing on maintaining the bubble in the center position of the bubble level as she punctured the tissue phantom and slowly advanced the 8 cm to the target.

Results of Experiment 2

In the second experiment, subjects demonstrated a 63% reduction in the number of passes required to hit an 8-cm target using a 45° angle approach with the position guidance device (P<0.0001) (FIG. 13). For each individual subject the position guidance device decreased the mean number of required passes 67-78%.

Figure 12:
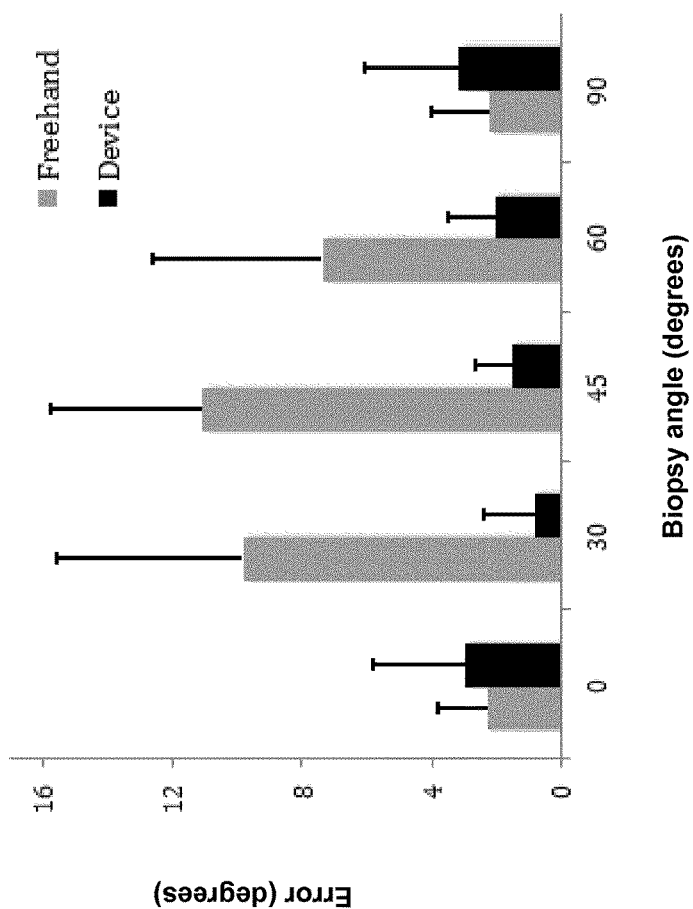
FIG. 12 illustrates the improved needle angle accuracy with use of the position guidance device at multiple typical biopsy angles.
Figure 14:
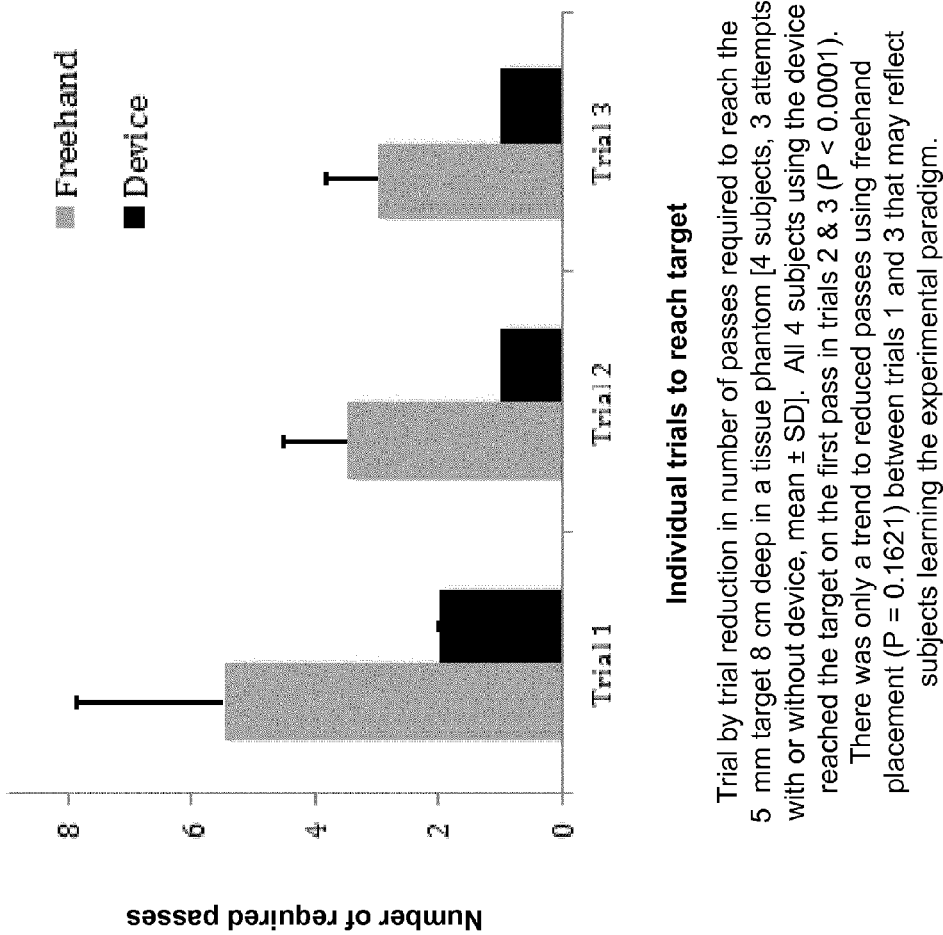
FIG. 14 illustrates the trial by trial reduction in number of passes required to reach the 5-mm target 8-cm deep in a tissue phantom with use of the position guidance device.

The initial angle error on the first needle pass also decreased 83% to 1.1°±0.7. This level of angle error reduction was consistent with the 86% reduction observed for the 45° target angle in the first experiment (FIG. 12).

Both freehand and device-assisted target experiments demonstrated a reduced number of passes with repeat trials, but freehand changes between trials 1 and 3 were not significant (P=0.1621). This may reflect subjects learning the experimental paradigm, but the magnitude of position guidance device assisted results were consistently higher (e.g. trial 3 freehand required 45% less passes than trial 1 freehand, however device-assisted trials 1 and trial 3 required 64% and 82% less passes respectively compared to freehand trial 1).

After the first trial, all four subjects only required one pass with the position guidance device to contact the 8-cm deep, 5-mm target using a 45° angle (e.g. 67% of all device attempts). In the first trial with the position guidance device, all subjects were observed to place the needle beyond halfway, then recognize with repeat CT imaging that the needle was at the correct angle (1.1° mean error). Subjects then just advanced the needle to the target on the second pass. The first pass needle depth reflected this increased confidence—the freehand depth did not vary between trials 1 and 3, whereas the position guidance device-assisted first pass depth increased to 7.6±0.6 cm on trials 2 and 3 (P<0.0001). In a post hoc trial of subject confidence with the position guidance device after completion of the two planned experiments, subjects C & D were asked to reach a target using a 30° angle device—both subjects achieved this on the first pass.

As demonstrated by the experimental results, using the position guidance device in a tissue phantom demonstrated objective improvements in needle placement accuracy, precision and efficiency. In particular, the position guidance device increased efficiency in an intermediate-difficulty CT-guided tissue biopsy simulation by 63%. These data suggest that in real patients the position guidance device could improve performance in radiologists with different levels of experience, and result in significant reductions to CT-guided procedure time, patient radiation exposure and tissue trauma.

Questionnaire

After completion of Experiment 1 and Experiment 2, the four subjects were given a brief questionnaire regarding ease of use of the position guidance device. The questionnaire results are shown in Table 2 below and demonstrate most notably that the position guidance device was easy to use and intuitive.

TABLE 2

Survey responses after completion of both experiments comparing freehand and position guidance device use in a tissue phantom of the four subjects (Score: mean ± SD]

| # | Survey questions | Score[+] |
|---|---|---|
| 1 | The concept for how the device works is easy to understand | 5.0 ± 0 |
| 2 | The device is easy to learn how to use | 5.0 ± 0 |
| 3 | The device increased my accuracy getting specific target angles | 5.0 ± 0 |
| 4 | The device increased my efficiency getting to the target capsule | 5.0 ± 0 |
| 5 | The device reduced tissue trauma from position adjustments | 4.8 ± 0.5 |
| 6 | The current bubble level sensitivity is too responsive | 3.8 ± 0.5 |
| 7 | I was slower placing the needle on a given pass with the device | 3.3 ± 1.5 |
| 8 | Horizontal target angles are harder than vertical target angles | 4.0 ± 0.8 |
| 9 | The device would make overall procedure times much shorter | 4.8 ± 0.5 |
| 10 | The device would reduce radiation to patients for CT procedures | 5.0 ± 0 |
| 11 | Use of the device would make procedures safer | 4.5 ± 0.6 |
| 12 | It would be easy to use the device in real patients | 4.3 ± 0.5 |
| 13 | If available I would use this device in procedures | 5.0 ± 0 |
| 14 | I would encourage colleagues to use this device | 4.8 ± 0.5 |

[+]Question response options were - strongly agree (5), agree (4), neutral (3), disagree (2), strongly disagree (1).

Figure 1:
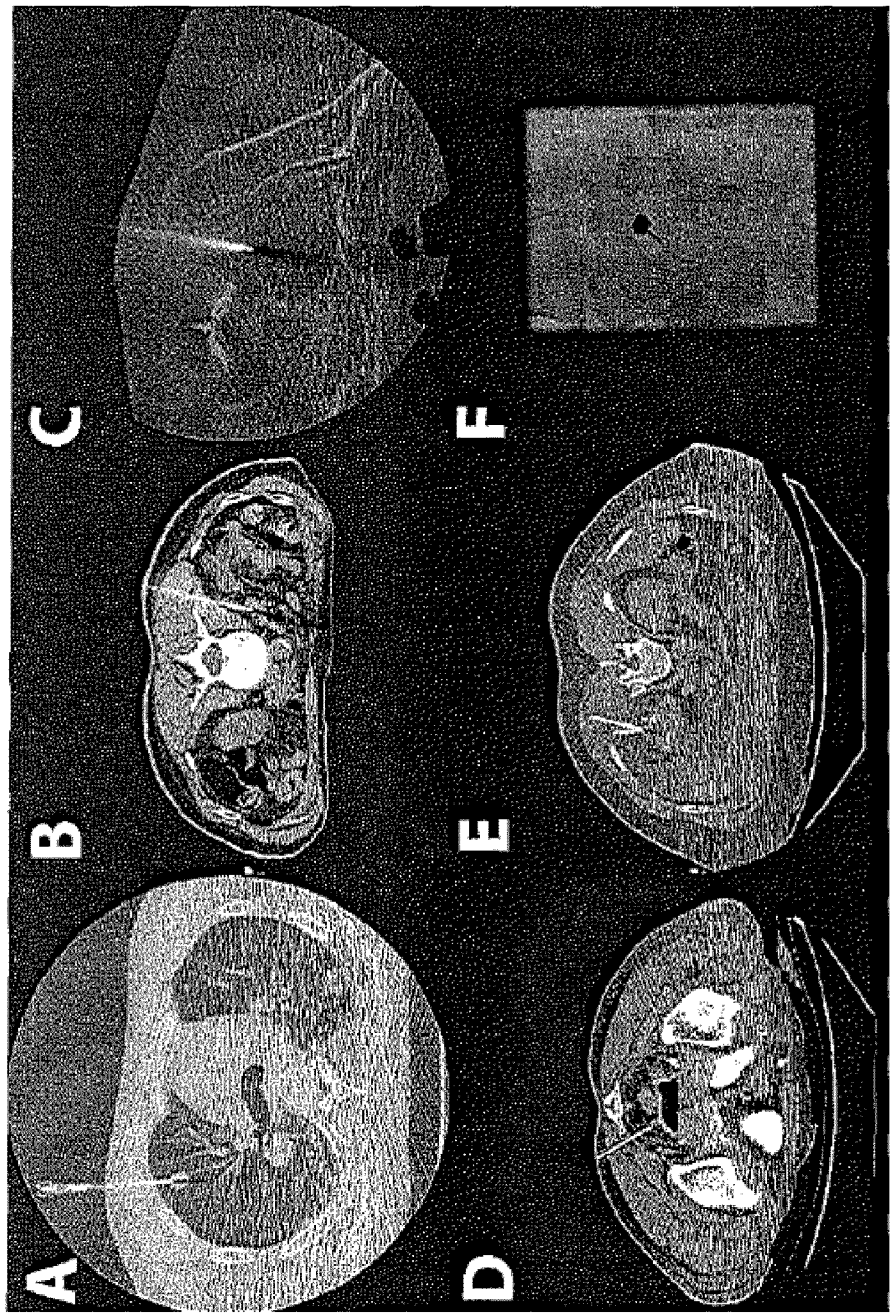
FIGS. 1A-1F illustrate various embodiments in which image guidance can be used for needle-based procedures

While most examples and schematics described herein have depicted CT-guided procedures, one of ordinary skill in the art will appreciate that the position guidance device 1 can also be applied to other image-guided procedures using fluoroscopy, ultrasound or magnetic resonance imaging (MRI). Besides various uses of lumbar puncture (e.g. diagnostic CSF studies, myeogram, intrathecal medical therapy, drain placement) (FIG. 1E), fluoroscopy guidance is still commonly used for spine and joint aspirations (contrast or steroid injections). The position guidance device 100 may also play a role in procedures without any imaging that rely on consistent anatomy, surface landmarks and appropriate needle position (e.g. traditional technique for central line placement or liver biopsy). Similarly, the position guidance device 100 may be used in surgical procedures such as minimally invasive surgical procedures. For example, it is possible that the position guidance device 100 may be used for correct laparoscopic anterior cruciate ligament graft placement (which is normally oriented oblique in multiple anatomic planes parallel to the intracondylar notch). In this example, a bubble level could be manufactured specifically for the medical application or specifically for individual patients (e.g. correct target angles in multiple planes for ligament replacement depending on patient's specific anatomy).

One of ordinary skill in the art will appreciate that application of the position guidance device is not limited to CT-guided procedures with needles. There may be broad applications using multiple variations of the position guidance device to procedures with or without image guidance across different medical specialties.

According to the configuration of the position guidance device 100 described in the embodiments above, an operator may be provided with immediate and intuitive visual feedback about correct needle position. Thus, the operator is provided with visual feedback immediately from a single visual reference (i.e., location of the air bubble) at the needle entry site without having to look away (for example, at an imaging device) as the needle is positioned. The bubble level 4 also allows the operator to eliminate unrealistic assumptions that the relationship between the patient and the needle will remain static throughout the procedure (i.e., that the patient will not move) by providing the visual feedback.

Because the bubble level 4 is a small modification to procedural needles 1 currently in use, the position guidance device 100 fits into the current skill set used for these procedures and is likely to accelerate the rate at which procedures can be completed without extensive additional training The simple features of the position guidance device 100 make it easy to manufacture and market in the fashion of other disposable equipment used during these procedures. The bubble level 4 is a lightweight, compact addition to the needle 100 that is designed for repeat imaging. In particular, the bubble level 4 allows the operator to see if the position guidance device 100 has been moved, especially in cases where repeat imaging is required and the patient must be placed into the CT scanner again. In addition, because the position guidance device 100 is compact, the position guidance device 100 can easily and repeatedly clear the inner bore of a scanner. Moreover, due to the size of the position guidance device 100, multiple needle placements may be performed simultaneously and in very close approximation to each other, which may reduce the total duration of the procedure. Because the bubble level 4 is lightweight, the needle 1 will not change positions if the position guidance device 100 is unsupported (i.e., if the operator lets go of the position guidance device 100).

In one implementation, the bubble level mechanism described above can generally be associated with a mechanical device. For example, devices such as drills, drivers, and the like, are used in applications requiring a particular angle or alignment similar to described above with regard to needles. Some of these devices incorporate a bubble level into the device that are either parallel or orthogonal to the device (for example, a bubble level parallel or orthogonal to a drill bit of a drill), but do not enable the user to achieve a target angle beyond perfect vertical or horizontal. By altering the angle with the use of a bubble level described in the embodiments above, oblique angles can be achieved for a variety of devices. Similar to the needle described above, the bubble level would not necessarily need to be incorporated into the device, but may be repeatedly and reversibly attached, for example, by an adhesive or hook and loop strip The construction and arrangements of the position guidance device, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, image processing and segmentation algorithms, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

What is claimed is:

1. A position guidance system for minimally invasive medical procedures comprising:
   a medical device having a first end configured for percutaneous insertion to a target and a second end configured to remain exterior to a patient's skin;
   a hub connection provided at the second end of the medical device;
   at least one bubble level including a bubble configured to provide a visual indication of a deviation from a target angle for medical device insertion; and
   a connector configured to reversibly and repeatedly connect the bubble level to the hub connection of the medical device,
   wherein when the bubble is positioned at a center of the bubble level, an actual insertion angle of the medical device is the same as the target angle, and when the bubble is positioned off-center of the bubble level, the actual insertion angle of the medical device deviates from the target angle, and
   wherein the target angle is an angle between the medical device and a straight line from the target.

2. The position guidance system of claim 1, wherein the medical device is a needle.

3. The position guidance system of claim 1, wherein the hub connection is a Luer-lock or a tuberculin hub fitting.

4. The position guidance system of claim 1, wherein the connector is an adhesive, hook and loop fastening, threading or snap system.

5. The position guidance system of claim 1, wherein the hub connection is hollow and configured to allow coaxial passage of fluid or other devices.

6. The position guidance system of claim 1, wherein the bubble level comprises a single tubular bubble level configured to detect an x-tilt error or a z-tilt error in the actual insertion angle.

7. The position guidance system of claim 1, further comprising a pivot connection between the hub connection and the connector, the pivot connection configured to allow the hub connection to pivot with respect to the bubble level to vary the target angle.

8. The position guidance system of claim 1, wherein the bubble level comprises a lightweight, sterile plastic housing containing a liquid and the bubble.

9. The position guidance system of claim 1, wherein the bubble level comprises a single bull's eye bubble level configured to detect an x-tilt error, a z-tilt error or a combination thereof.

10. The position guidance system of claim 1,
    wherein the bubble level comprises a single dynamic bubble level configured to detect an x-tilt error or a z-tilt error, and
    wherein the single dynamic bubble level comprises an arcuate housing containing a liquid and the bubble.

11. The position guidance system of claim 1, wherein the target angle is fixed at an angle from 0 to 90 degrees.

12. The position guidance system of claim 1, further comprising off-center hash marks disposed at positions on the bubble level indicative of a predetermined deviation from the target angle.

13. The position guidance system of claim 1, further comprising two bubble levels,
    wherein a first bubble level comprises a tubular bubble level, and
    wherein a second bubble level is selected from the group consisting of a tubular bubble level, a bull's eye bubble level, and a dynamic bubble level.

14. The position guidance system of claim 1, wherein the bubble level is an air bubble level.

15. The position guidance system of claim 1, wherein the straight line is a vertical line from the target.

16. A position guidance system for minimally invasive medical procedures comprising:
    a medical device having a first end configured for percutaneous insertion and a second end configured to remain exterior to a patient's skin;
    a hub connection provided at the second end of the medical device;
    at least one bubble level including a bubble configured to provide a visual indication of a deviation from a target angle for medical device insertion; and
    a connector configured to reversibly and repeatedly connect the bubble level to the hub connection of the medical device,
    wherein when the bubble is positioned at a center of the bubble level, an actual insertion angle of the medical device is the same as the target angle, and when the bubble is positioned off-center of the bubble level, the actual insertion angle of the medical device deviates from the target angle, and wherein a weight of the bubble level is selected such that a position of the medical device does not change if the position guidance system is not fully supported.

17. A method for using a position guidance system for minimally invasive medical procedures comprising:
selecting a target angle for medical device insertion based on initial images obtained;
attaching a bubble level having a bubble configured to provide a visual indication of a deviation from the target angle to a medical device configured for use in a percutaneous image-guided procedure, the target angle being an angle between the medical device and a straight line from a target;
adjusting a position of the medical device such the bubble remains in a center of the bubble level,
wherein when the bubble is positioned at the center of the bubble level, an actual insertion angle of the medical device is the same as the target angle, and when the bubble is positioned off-center of the bubble level, the actual insertion angle of the medical device deviates from the target angle.

18. The method of claim 17, further comprising varying the target angle by pivoting the medical device with respect to the bubble level via a pivot connection between the medical device and the bubble level.

19. The method of claim 17, wherein the straight line is a vertical line from the target.

* * * * *